United States Patent [19]

Riester

[11] Patent Number: 4,643,171

[45] Date of Patent: Feb. 17, 1987

[54] METHOD OF MANUFACTURING AN OTOSCOPE

[75] Inventor: Karlheinz Riester, Juningen, Fed. Rep. of Germany

[73] Assignee: Rudolf Riester GmbH & Co. KG Fabrik med. Apparate, Juningen, Fed. Rep. of Germany

[21] Appl. No.: 724,194

[22] Filed: Apr. 17, 1985

[30] Foreign Application Priority Data

Apr. 18, 1984 [DE] Fed. Rep. of Germany ....... 3414730

[51] Int. Cl.$^4$ .............................................. A61B 1/22
[52] U.S. Cl. ...................................................... 128/9
[58] Field of Search ............................................. 128/9

[56] References Cited

U.S. PATENT DOCUMENTS

| | | | |
|---|---|---|---|
| 1,515,771 | 11/1924 | Greenwald | 128/9 |
| 2,154,885 | 4/1939 | Arnesen | 128/9 |
| 3,384,076 | 5/1968 | Speelman | 128/9 |
| 3,728,998 | 4/1973 | Heine | 128/9 |
| 3,934,578 | 1/1976 | Heine | 128/9 |
| 4,006,738 | 2/1977 | Moore et al. | 128/9 |
| 4,366,811 | 1/1983 | Riester | 128/9 |

FOREIGN PATENT DOCUMENTS 3009876 9/1981 Fed. Rep. of Germany .

Primary Examiner—William H. Grieb
Attorney, Agent, or Firm—Holman & Stern

[57] ABSTRACT

The invention relates to a method of manufacturing an otoscope, according to which method the component parts of the otoscope can be assembled with particular ease. In order to achieve this, a prefabricated fiber optics assembly is employed, and the otoscope is configured such that all the parts can be inserted in sequence from one side of the housing head into an accommodation opening of the housing head.

9 Claims, 13 Drawing Figures

METHOD OF MANUFACTURING AN OTOSCOPE

BACKGROUND OF THE INVENTION

The invention relates to a method of manufacturing an otoscope with a fiber-optic ring-shaped light Commonly an otoscope is comprised of a hand grip which also accommodates batteries, a housing head for a physician to look through and see the field of examination, a mount for a disposable funnel at the forward end of the housing head, and a loupe (magnifying lens) at the back of the housing head. The field of examination is illuminated by an electric bulb which is disposed at the transition between the battery-grip and the housing head. The light beam given off by the bulb must be bent onto the field of examination. The simplest way of accomplishing this is with optical fibers.

The assembly of the entire device is as a rule complex, time consuming and expensive. As a rule the housing head is manufactured first, then the fiber optics are positioned on it and are permanently mounted by means of a plastic resin adhesive. Only then can the fiber optics be covered, the housing head be attached to the battery-grip, and finally the loupe be added to the housing head. In this process, if the fiber optics are improperly positioned, the entire housing head becomes scrap or at least must be reprocessed. This further adds to costs.

Pressurized air is used with otoscopes, for certain examination procedures. This air passes into the interior of the otoscope and has the tendency to lift the pivoted loupe off of its mount. In order to prevent this, there have been employed complex latch systems which further add to the manufacturing cost.

SUMMARY OF THE INVENTION

It is an object of the invention to improve the manufacture of otoscopes, and to provide an otoscope in which the manufacturing drawbacks of the prior art are avoided, while preserving convenience of use for the physician along with operating safety and stability.

In a method according to the invention, first the housing head of the otoscope, provided with an opening extending through it, is attached to the battery-grip. This facilitates handling for the following steps, but was not possible as a first step in the prior art bacause it was first necessary to attach the fiber optics. In the next step a prefabricated fiber optics assembly is moved up in the direction of the axis of the ring-shaped illumination means formed by said optics, inserted into the opening passing through the housing head, and there fixed in place. In contrast to the prior art, the fiber optics assembly no longer surrounds the housing head on the outside of said housing head. Rather, it is mounted interiorly of the head, being in the form of a prefabricated assembly. The prefabricated unit can thus be manufactured without interference from the other requirements of the otoscope, and is easy to handle in assembling the otoscope, so that substantially no manufacturing bottlenecks occur. After the mounting of the fiber optics assembly, the loupe is attached to the housing head.

The assembly process is particularly simple and easy if the fiber optics assembly is inserted into the main opening through the housing head from the side of said head which faces away from the direction of examination (i.e., from the rear of the head). Since the disposable funnel is generally conical in shape, and likewise therefore the prefabricated fiber optics assembly has a diameter which decreases forwardly, this direction of assembly is particularly convenient. With this arrangement, an appropriate stop member may be provided in the opening of the housing head, to quickly and easily position the prefabricated fiber optics assembly.

Alternatively, it is possible, particularly when the device is assembled in a lying-down position, to insert the prefabricated fiber optics assembly from the front of the housing head, i.e. into the housing head from the side of the housing head which faces the direction of examination, and then to attach the fiber optics assembly in the housing head.

Further simplification of the assembly process results if, when using a stop member in the housing head to position the prefabricated fiber optics assembly, the connection to the housing head is made not with the fiber optics but with a cover for the fiber optics assembly which cover is attached to the housing head in a mounting cavity provided in the head for mounting the fiber optics. Advantageously, this connection is accomplished by bolting or screwing, so that the fastening bolt or screw may also act as a pivot for swinging the loupe. Alternatively the connection may be by adhesive fastening.

It is particularly advantageous when applying the cover for the fiber optics assembly, to accommodate catches for the loupe. The cover will also cover axial blind holes provided in the housing head to accommodate springs which have been installed therein, whereby spherical catches will be subsequently installed which press against the springs; with corresponding circular holes being provided in the cover, the spring-loaded catches engaging corresponding catch recesses in the loupe.

The funnel-ejector may also be fixed and guided via the cover. The ejector extends from the front part of the housing head where a support means for the disposable funnel is provided, through the entire housing head and the cover, to the rear of the device, where an actuating head for the spring-loaded funnel-ejector projects beyond the cover.

The appearance of the completed device is improved if the cover also extends over the head of a set screw employed to attach the housing head to the battery-grip. In this case provision should be made to enable the set screw to be screwed in sufficiently to clear the space in the housing head which will receive the cover; and this should be able to be done before the fiber optics assembly is inserted.

In the application of pressurized air, which can lead to a certain increase of pressure in the interior of the viewing path of the otoscope, in the prior art the loupe would often be forced backward, thereby interfering with the observation of the examination field. Attempts have been made to prevent this by employing relatively costly locking devices, which also tend to complicate the manufacturing process. Nonetheless, the pressure still often dislodged the loupe from the locking means.

Another disadvantage of the loupe arrangement in known otoscopes is that the loupe must be held by the operator when in the open position, because it has a tendency to fall back over the observation opening. This makes it more difficult for the user to handle the otoscope.

According to a further feature of the invention, provision is made for retaining the loupe in the open position. In particular, the loupe is provided with a latch recess near its pivot axis, and a spring-loaded spherical catch is provided diametrically opposite thereto. As a result, when the loupe is swung by 180 degrees, the latch recess engages the catch, whereby the loupe is fixed in this 180 degree upswung position.

Operation of the otoscope is further facilitated if a similar latch arrangement is provided for the loupe when in the closed position. Advantageously, this closed-position latch may be disposed at a substantial distance from the pivot axis of the loupe.

To ensure that the loupe is secured in a position normal to the optical axis, means are provided which are extremely easy to manufacture but are nonetheless highly effective. A prism-shaped undercut member is provided on the housing head or on the cover, and the lower edge of the loupe remote from the pivot axis of the loupe is provided with a matching bevel. It is particularly advantageous if the undercut member has an arcuate shape to correspond to the swing path of the loupe, so that the loupe is secured against being lifted from its normal closed position not just at a single securing point but along a relatively large surface.

Further details, advantages, and features of the invention will be apparent from the following description and claims, read in conjunction with the attached drawings.

DESCRIPTION OF PREFERRED EMBODIMENT

Figure 1:
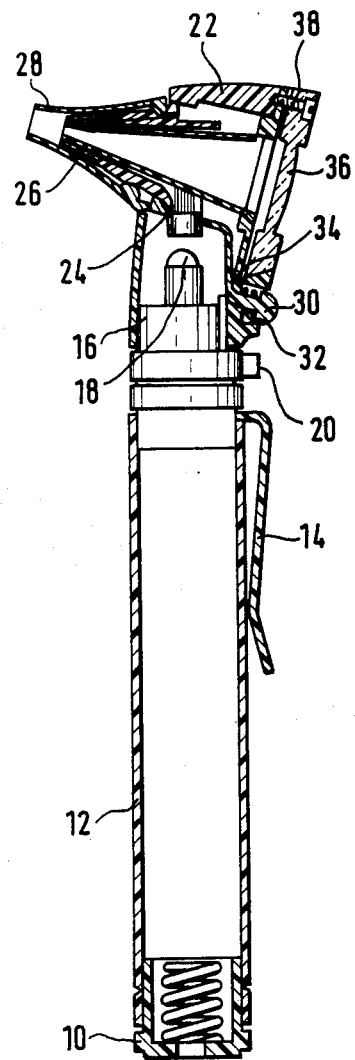
FIG. 1 is a sectional elevation of an otoscope in accordance with the invention.

FIG. 1 shows an otoscope having a battery grip 12 which is closed at its lower end by a closure cap 10 and which carries a clip 14. On the upper end of the grip 12 an adapter 16 (FIG. 1) is provided for attaching an incandescent bulb 18 into a socket. An adjusting ring 20 is also provided, to adjust the intensity of illumination.

A housing head 22 is rigidly attached to the upper end of the battery grip 12. The interior of the housing head 22 accommodates a glass-fiber fiber optics assembly 24 which will be described in more detail infra, and which forms a ring-shaped illumination means in cooperation with bulb 18. Further, a metal funnel 26 is integrated into the fiber optics assembly 24. A disposable funnel 28 can be pushed into place onto and held in place on said metal funnel. The disposable funnel 28 is ejectable from the metal funnel 26 with the aid of a funnel-ejector 30. To accomplish ejection, the ejector 30 is actuated against the action of compression springs 32.

Figure 5F:
FIG. 5a to 5f are various views of a funnel ejector employed in the device.
Figure 5A:
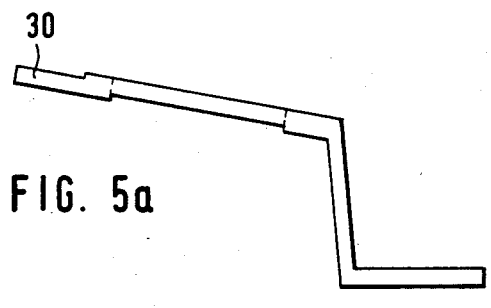
Figure 5E:
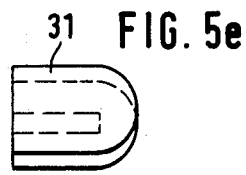
Figure 5B:
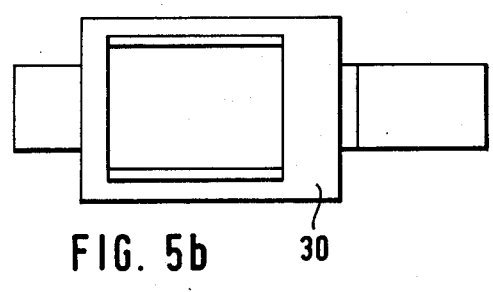
Figure 5D:
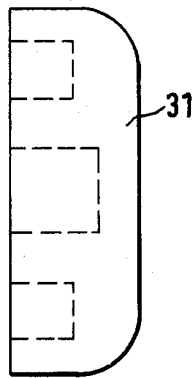
Figure 5C:
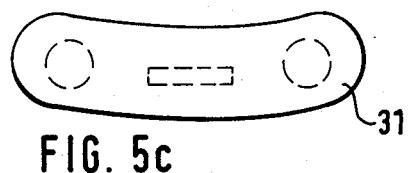

The funnel-ejector 30 is provided with an ejection actuating head 31 of arcuate form, see FIG. 5c. An arcuate opening 33 is provided in a cover 34, through which opening the actuating head may move in the housing head 22. Cover 34 serves to hold the fiber optics assembly 24 with associated parts in the housing head 22. Also provided in cover 34 are circular openings 35 into which spherical catches (described infra) can move.

Figure 2:
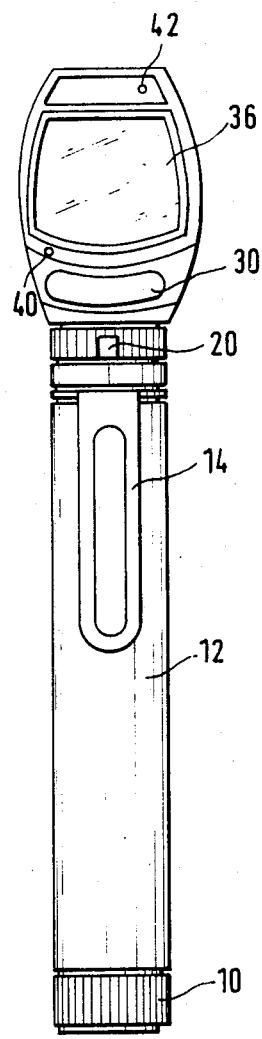
FIG. 2 is a rear elevational view of the otoscope of FIG. 1.

FIG. 2 shows how a loupe 36 is fixed at two latch points 40 and 42, with latch point 40 serving to fix the loupe in its operating position and latch point 42 serving to fix it in an upwardly pivoted position; as will be discussed in more detail infra with reference to FIG. 7.

Figure 3:
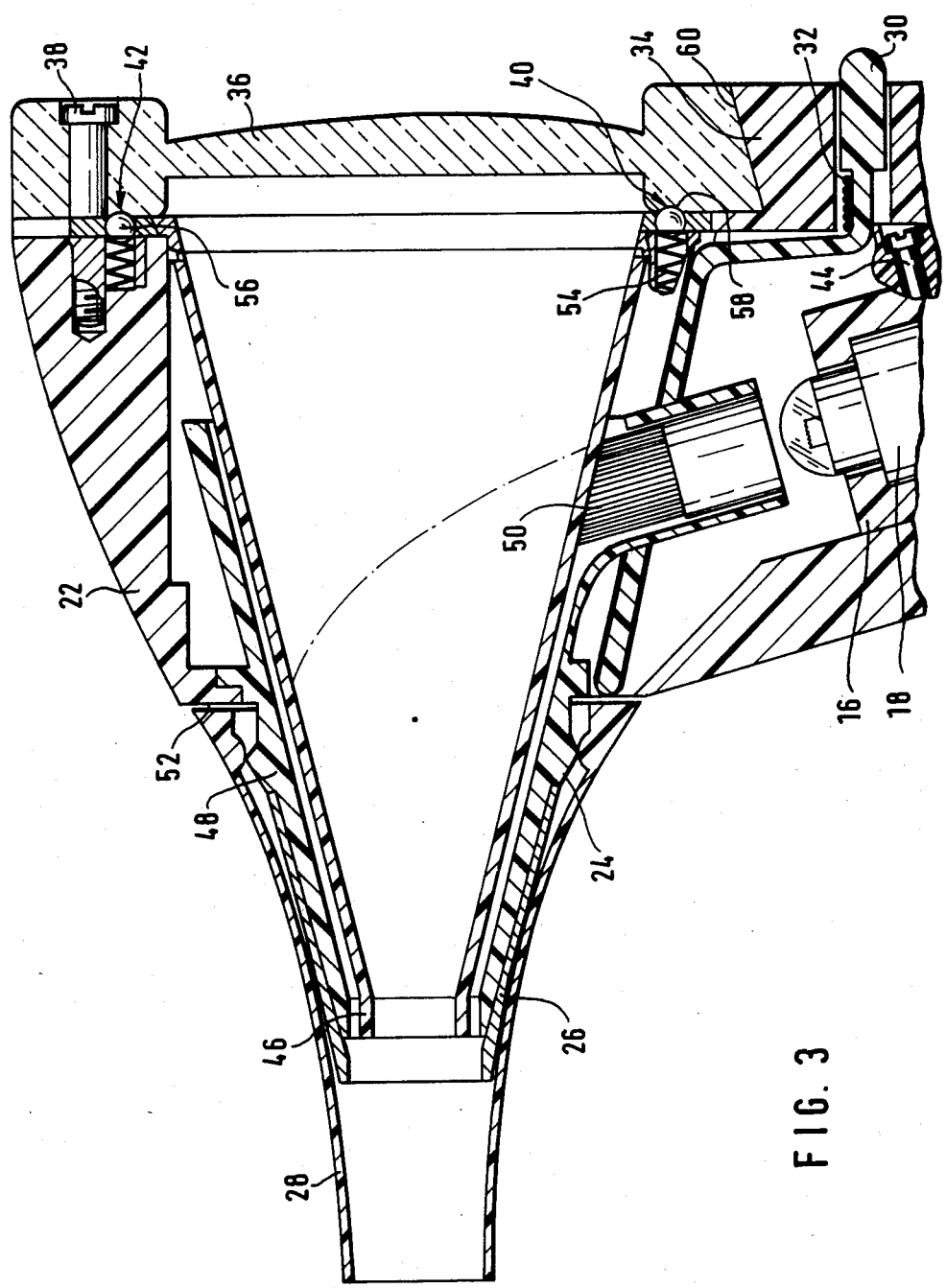
FIG. 3 is an enlarged cross section of a fully assembled housing head portion of the otoscope.

FIG. 3 is a more detailed view of the head of the otoscope. A set screw 44 serves to attach the housing head 22 to the battery grip 12. The prefabricated fiber optics assembly 24 consists of an interior funnel 46, an exterior funnel 48, funnel 48 being in turn covered on its outer side by the metal funnel 26; and a fiber bundle 50 which is passed (as shown by the dashed line) from a cylindrical fitting on the exterior funnel 48 at a space in front of the light bulb 18, into a gap between the interior and exterior funnels 46 and 48, to terminate in a ring configuration parallel to the viewing axis, thereby forming a ring-shaped illumination means for illuminating the examination field. The fiber optics assembly 24 comprised of all the parts 46, 48, 50 is prefabricated, and can be installed in the device as a unitary item.

The disposable funnel 28 can be applied onto the forward end of the prefabricated fiber obtics assembly 24 from the front, whereby it is fixed to the fiber optics assembly by simple catch means engaging a ring-shaped projection on the rear of the fiber optics assembly. The funnel-ejector 30 serves to eject the disposable funnel as will be discussed in more detail infra with reference to FIG. 5. For ejection, the ejector 30 is pressed forward against the action of a compression spring 32, whereby the disposable funnel 28 is moved over its catch and is ejected forwardly. The user may facilitate the ejection of the disposable funnel 28 by holding the device with the funnel axis extending downwardly, while actuating the ejection. This facilitates direct ejection of the disposable funnel 28 into a waste receptable.

The fiber optics assembly 24 is located in the housing head 22 by means of detent member 52 which is in the form of a step-shaped recess in the interior of the housing head 22, and which advantageously may be comprised of plastic material (as may in general all parts of the otoscope for which a material is not specified). The fiber optics assembly 24 may be pressed against the detent member 52 by means of the cover 34 which is in the form of a plate with augmented thickness in its region near or toward the battery-grip. The cover 34 also covers the set screw 44, which is screwed into the grip from the recess in the head which receives the cover 34.

It is also evident in FIG. 3 how the latch points 40 and 42 are constructed. Blind holes are extended into the housing head 22 parallel to the viewing axis, from the recess in the head for receiving the cover 34. These holes receive compression springs 54 bearing spherical catches 56 on their respective outer ends. Corresponding holes are provided in the cover 34, extending through said cover, so that the spring-loaded catches project beyond the rear surface of the cover 34.

Corresponding catch recesses 58 are provided in the loupe 36, on the forward face of the loupe which is directed toward the cover 34. The catches 56 engage in said recesses to fix the loupe in respective predetermined positions in its swinging path around a screw 38 which pivotally secures the loupe to head 22.

An important feature is an undercut member 60 which is provided on the cover 34 at the point at which it engages the edge of the loupe 36 remote from the swing axis of the loupe. The configuration of the undercut 60 is that of a conical surface tapering in the opposite direction to the interior funnel 46 for example. The lower edge of the loupe is also provided with a conical surface which matches that of the undercut 60. This undercut configuration holding the loupe reliably prevents the loupe, when the loupe is in the swung down position shown in FIG. 3, from moving back against the user's eye. In particular, the loupe is held on top by the screw 38, and on the bottom by the undercut 60 into which the edge of the loupe 36 fits.

Figure 4:
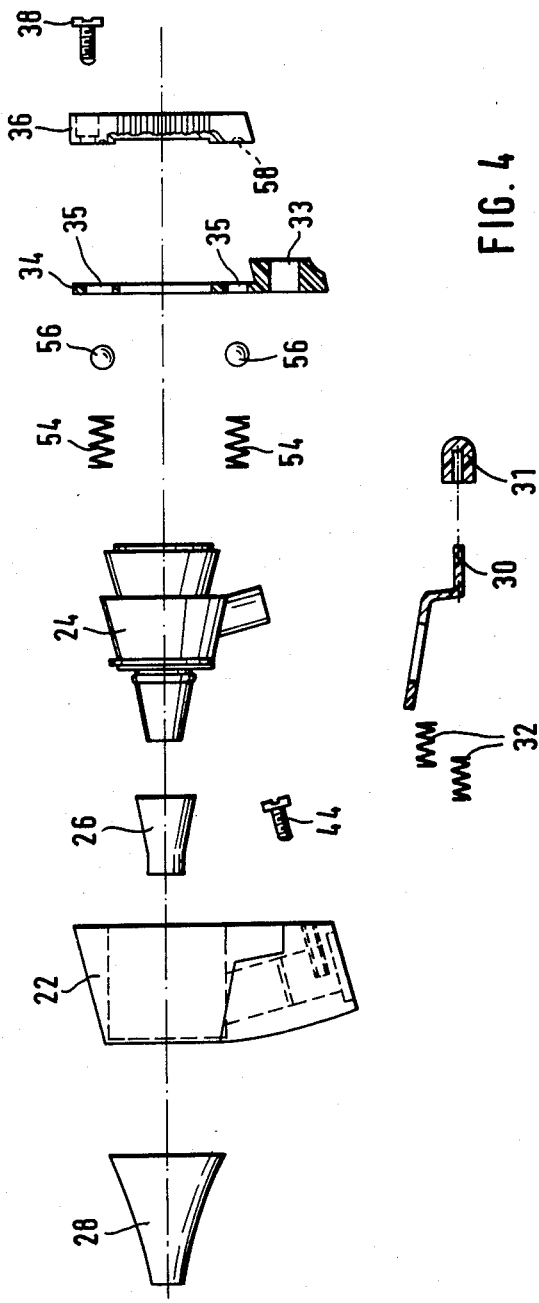
FIG. 4 is an exploded view which illustrates the assembly of the device.

FIG. 4 shows how the individual parts can be assembled in a facilitated manufacturing method. First, the housing head 22 is attached to the battery-grip 12 (not shown in Fig. 4) with the aid of the set screw 44. Thus mounting the housing head facilitates the further handling of the housing head during assembly. The prefabricated fiber optics assembly 24 is then inserted into the interior of the opening which extends entirely through the housing head 22. If the metal funnel 26 has not yet been integrated with the fiber optics assembly, this is done prior to inserting the fiber optics assembly; i.e., the metal funnel 26 is mounted on or applied onto the exterior funnel 48 (See FIG. 3) of the fiber optics assembly 24.

Depending on the particular structure, the funnel ejector 30 may be inserted after the insertion of the fiber optics assembly or along with it. In order to accomplish this, it is sufficient to first insert the compression springs 32 into the appropriate recesses in the housing head 22, then to insert the ejector 30, with its central opening, over the cylindrical projection on the exterior funnel 48, then to reinsert the whole assembly into the housing head 22 which is advantageously held with its front end directed downwards. The broad, arcuately curved ejector actuating head 31 is then applied to the funnel ejector 30, or has been previously mounted thereon.

The next assembly step is to insert the compression springs 54 in the above-mentioned blind holes in the housing head 22, and to apply the catches 56 to the springs 54. Then the cover 34 is brought in position by moving it forward from a position to the rear of the head 22, the loupe 36 is applied over the cover 34, and the entire subassembly comprising the cover and loupe, with the springs 54 and catch spheres in place is attached to the housing head 22 with the aid of the screw 38. The cover 34 has circular openings 35 with diameters slightly less than the diameters of the corresponding catches 56. The catches 56 are urged rearwardly to engage the corresponding catch recesses 58 in the loupe 36, via the compression spring 54 which extend through the perforations 35. The cover 35 is thicker at its portion remote from the pivot axis of the loupe, and said portion is undercut at 60 and has an arcuate opening 33 through which the ejector actuating head 31 of the funnel ejector 30 projects, so that the user can conveniently access the actuating head. Advantageously, the physician can thus use his thumb to actuate the ejector.

It is seen that all the parts are installed in the housing head in sequence from the rear; when a prefabricated fiber optics assembly 24 is employed, this arrangement accordingly results in an assembly process which is considerably simplified over the prior art.

For completeness, FIG. 4 also shows the disposable funnel 28, which can be applied from the front after the above assembly procedures. The disposable funnel is applied to the mount provided therefor on the fiber optics assembly 24 or on the housing 22.

FIG. 5 shows more details of the structure and assembly of the funnel ejector 30. It may be seen that the ejector consists essentially of a curved, blanked and/or punched and/or stamped piece of sheet metal, which is bent to match the open spaces within the housing head 22. In the side view of FIG. 5a the nearly vertical side can be clearly seen, against which side the ejector compression springs 32 can act to return the funnel ejector 30 to its rest position after actuation of the ejector. FIG. 5b shows the framelike structure of the funnel ejector 30 in its central section; in particular it has a central opening for the fiber optics assembly and/or a hollow cylindrical projection on the exterior funnel 48 of the fiber optics assembly 24 to pass through said framelike structure with adequate room. FIG. 5f indicates how said segment is arcuately curved so as to conserve space in the housing head.

FIGS. 5c, 5d, and 5e show the ejector actuating head which is appropriately configured for thumb actuating and is comprised of a plastic material. This head can be pushed or molded onto the rear end of the funnel ejector.

Figure 6:
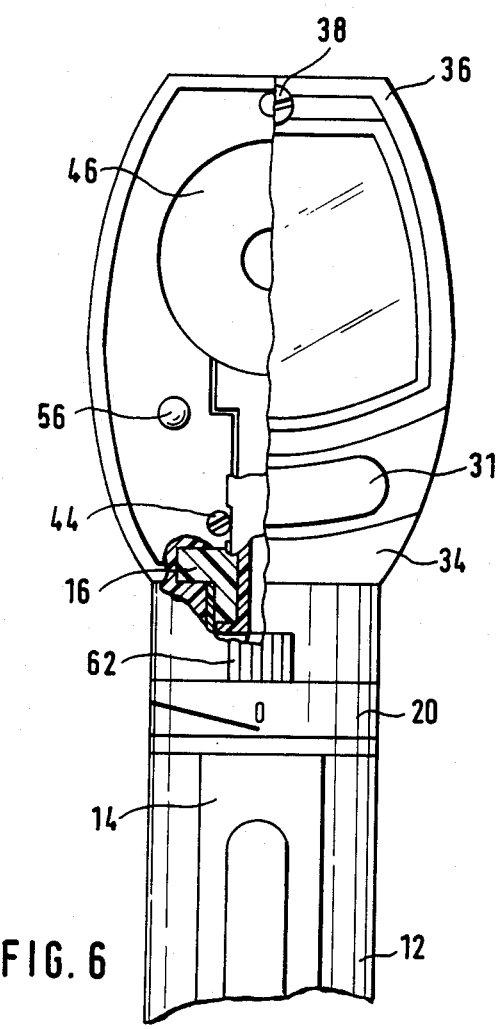
FIG. 6 is a partially cut away rear view of the housing head of the otoscope enlarged with respect to FIG. 2.

The right half of FIG. 6 is the rear view of the device with the loupe 36 in the closed position. The left half shows the device with the loupe removed, and looking into the interior funnel 46. The battery switch 62 is also visible, which switch is mounted on the upper end of the battery-grip 12 by means of the adjusting ring 20.

Figure 7:
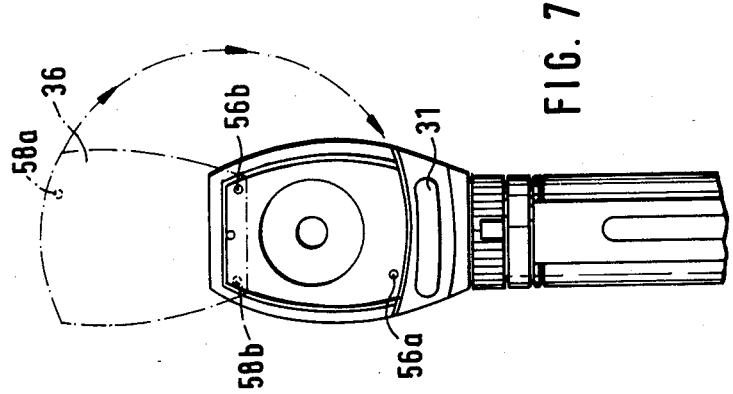
FIG. 7 is a rear view of the otoscope showing the possible positions into which the loupe may be swung.

FIG. 7 shows the disposition of the latch points for the loupe. Catch 56a together with catch recess 58a serves to hold the loupe 36 in the closed position, wherein the loupe is engaged by the undercut configuration 60. The loupe is swung into this closed position via the path indicated by the arrows. The open position of the loupe is indicated in dashed line. The loupe 36 is also fixable in this position, with the aid of the catch 56b which is coordinated with the catch recess 58b in the loupe. (For the sake of illustration, the recess 58b is shown to the left of the center line of the device, in the position in which it is located when the loupe is in its closed position.)

Figure 8:
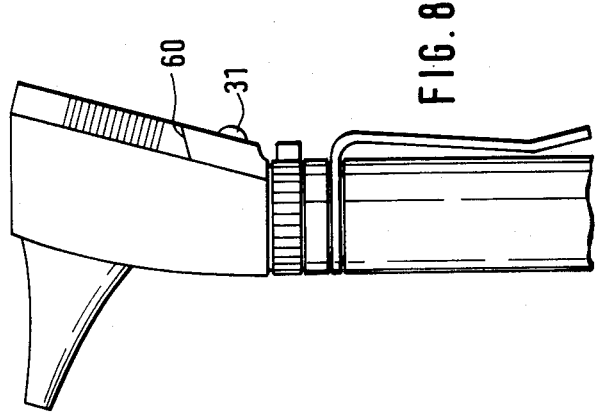
FIG. 8 is a side view of the otoscope illustrating the means by which the loupe is held in place.

FIG. 8 shows that the undercut 60 is preferably at an angle of 15 degrees to a plane normal to the plane of the loupe 36.

While only a preferred embodiment of the invention has been described herein in detail, the invention is not limited thereby, and modifications can be made within the scope of the attached claims.

I claim:

1. A method of manufacturing an otoscope having a housing head provided with fiber optics assembly and loupe, the housing head being attached to a battery-holding grip member; the method comprising attaching the housing head, provided with an opening extending there-through to the battery-holding, grip, providing a prefabricated fiber optics assembly of funnel means and a fiber optics bundle associated therewith, inserting the assembly into the opening passing through the housing head, fixing the assembly in place therein, and attacing the loupe to the housing head, wherein prior to inserting the prefabricated fiber optics assembly into the housing head, a funnel ejector is assembled with the fiber optics assembly, and both parts are then inserted into the housing head together.

2. The invention according to claim 1 wherein the prefabricated fiber optics assembly is introduced into the opening passing through the housing head from the rear of the head.

3. The invention according to claim 1 wherein the prefabricated fiber optics assembly when introduced into the housing head is engaged against a stop member.

4. The invention according to claim 3 wherein the prefabricated fiber optics assembly is fixed in the housing head by means of a cover.

5. A method according to claim 4 wherein the cover is attached to housing head by screw means.

6. The invention according to claim 5 wherein the loupe is also attached to the housing head by the screw means which forms a pivot for the loupe.

7. The invention according to claim 4 wherein, after insertion the fiber optics assembly but prior to the attachment of the cover springs and spherical catches are introduced into axial blind holes of the housing head for holding the cover in position, which catches extend through openings in the cover into catch recesses in the loupe.

8. The invention according to claim 2 wherein a set screw is screwed in from the opening in the housing head which accommodates the cover, said set screw serving to attach the housing head to the battery-holdng grip, prior to the insertion of the fiber optics assembly.

9. An otoscope manufactured by a method as claimed in claim 1.

* * * * *